(12) United States Patent
Laikos et al.

(10) Patent No.: US 11,318,507 B1
(45) Date of Patent: May 3, 2022

(54) RECEPTACLE CLEANING SYSTEM

(71) Applicants: Peter Laikos, Wadsworth, OH (US); Alexander Laikos, Wadsworth, OH (US)

(72) Inventors: Peter Laikos, Wadsworth, OH (US); Alexander Laikos, Wadsworth, OH (US)

(*) Notice: Subject to any disclaimer, the term of this patent is extended or adjusted under 35 U.S.C. 154(b) by 172 days.

(21) Appl. No.: 16/988,299

(22) Filed: Aug. 7, 2020

(51) Int. Cl.
| | |
|---|---|
| *B08B 9/093* | (2006.01) |
| *B65F 7/00* | (2006.01) |
| *A61L 2/18* | (2006.01) |
| *B05B 13/04* | (2006.01) |
| *B05B 13/06* | (2006.01) |
| *A61L 2/22* | (2006.01) |
| *B65F 1/14* | (2006.01) |
| *A61L 11/00* | (2006.01) |

(52) U.S. Cl.
CPC .............. *B08B 9/0936* (2013.01); *A61L 2/18* (2013.01); *A61L 2/22* (2013.01); *B05B 13/0421* (2013.01); *B05B 13/0636* (2013.01); *B65F 7/00* (2013.01); *B65F 7/005* (2013.01); *A61L 11/00* (2013.01); *B08B 2209/08* (2013.01); *B65F 1/14* (2013.01)

(58) Field of Classification Search
CPC .... B65F 7/00–005; B05B 1/00–17/085; B08B 9/08–46; B08B 9/027–035; B08B 1/00–17/065; A61L 11/00; A61L 2/00–33/18; B60S 3/04–066
See application file for complete search history.

(56) References Cited

U.S. PATENT DOCUMENTS

| | | | | |
|---|---|---|---|---|
| 1,838,634 | A * | 12/1931 | Peterson | ................. B08B 9/093 134/167 R |
| 3,985,572 | A | 10/1976 | Peterman | |
| 5,301,702 | A * | 4/1994 | McKinney | ............... B08B 9/093 134/107 |
| 2002/0144714 | A1 | 10/2002 | McCasker | |
| 2008/0289665 | A1* | 11/2008 | Dwyer | .................... B65F 3/046 134/104.4 |

* cited by examiner

*Primary Examiner* — Mikhail Kornakov
*Assistant Examiner* — Richard Z. Zhang
(74) *Attorney, Agent, or Firm* — Sanchelima & Associates, P.A.; Christian Sanchelima; Jesus Sanchelima

(57) ABSTRACT

A portable spray cleaning system with a device for sanitizing the interior surface of residential trash cans. The device includes adjustable arms, a plurality of spray nozzles, and rubber clamps. On one end, the device may also include a port for connecting to a water supply via a hose. Once the hose is connected, water can then be sprayed out through the spray nozzles. The pressure created by the water flow enables the device to rotate while water is being sprayed. There may also be a compartment for inserting a disinfectant that mixes in with the water. The device is collapsible for easy storage and packaging. It is known that trash receptacles often become very dirty and contaminated after repeated use.

11 Claims, 4 Drawing Sheets

RECEPTACLE CLEANING SYSTEM

BACKGROUND OF THE INVENTION

1. Field of the Invention

The present invention relates to a cleaning device and, more particularly, to a receptacle cleaning device with a spinning arm that mounts a top end of a trash receptacle to deliver a deep cleaning to an interior surface of the trash receptacle.

2. Description of the Related Art

Several designs for a cleaning device have been designed in the past. None of them, however, include a portable spray cleaning system with a device for sanitizing the interior surface of residential trash cans. The device includes adjustable arms, a plurality of spray nozzles, and rubber clamps. On one end, the device may also include a port for connecting to a water supply via a hose. Once the hose is connected, water can then be sprayed out through the spray nozzles. The pressure created by the water flow enables the device to rotate while water is being sprayed. There may also be a compartment for inserting a disinfectant that mixes in with the water. The device is collapsible for easy storage and packaging. It is known that trash receptacles often become very dirty and contaminated after repeated use. It is also known that this contamination may lead to harmful bacteria that may infect individuals. Therefore, there is a need for a receptacle cleaning device that will effortlessly clean the interior of a trash receptacle. This will allow individuals and families to continue using their trash receptacles while reducing their risk of being exposed to harmful bacteria.

Applicant believes that a related reference corresponds to U.S. Pat. No. 3,985,572 issued for an automatic spray cleaning apparatus and method. The cited disclosure comprises an automatic high-pressure spray cleaning apparatus and method for rapidly and efficiently removing material coated on the surface of an object. Applicant believes that another related reference corresponds to U.S. patent publication No. 2002/0144714 issued for a rotary cleaning apparatus. The publication discloses a support frame mounted to a rotor assembly having at least one spray arm and at least one jet spray nozzle located on the spray arm. However, the cited references differ from the present invention because they fail to disclose a collapsible trash can cleaner with adjustable arms, a plurality of spray nozzles, rubber clamps, a port for connecting a hose, a compartment for adding disinfectant and the ability to rotate under water pressure. The combination of these elements is not disclosed in the cited references and provide the most effective cleaning for a trash receptacle.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a receptacle cleaning device which aids in maintaining a clean and safe to use trash receptacle for a household.

It is another object of this invention to provide a receptacle cleaning device which has a cross shaped configuration with adjustable arms configured to fit over most existing trash receptacles.

It is still another object of the present invention to provide a receptacle cleaning device which includes a spinning arm which sprays a combination of soap and water to deliver an effective wash to the interior of a trash receptacle.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
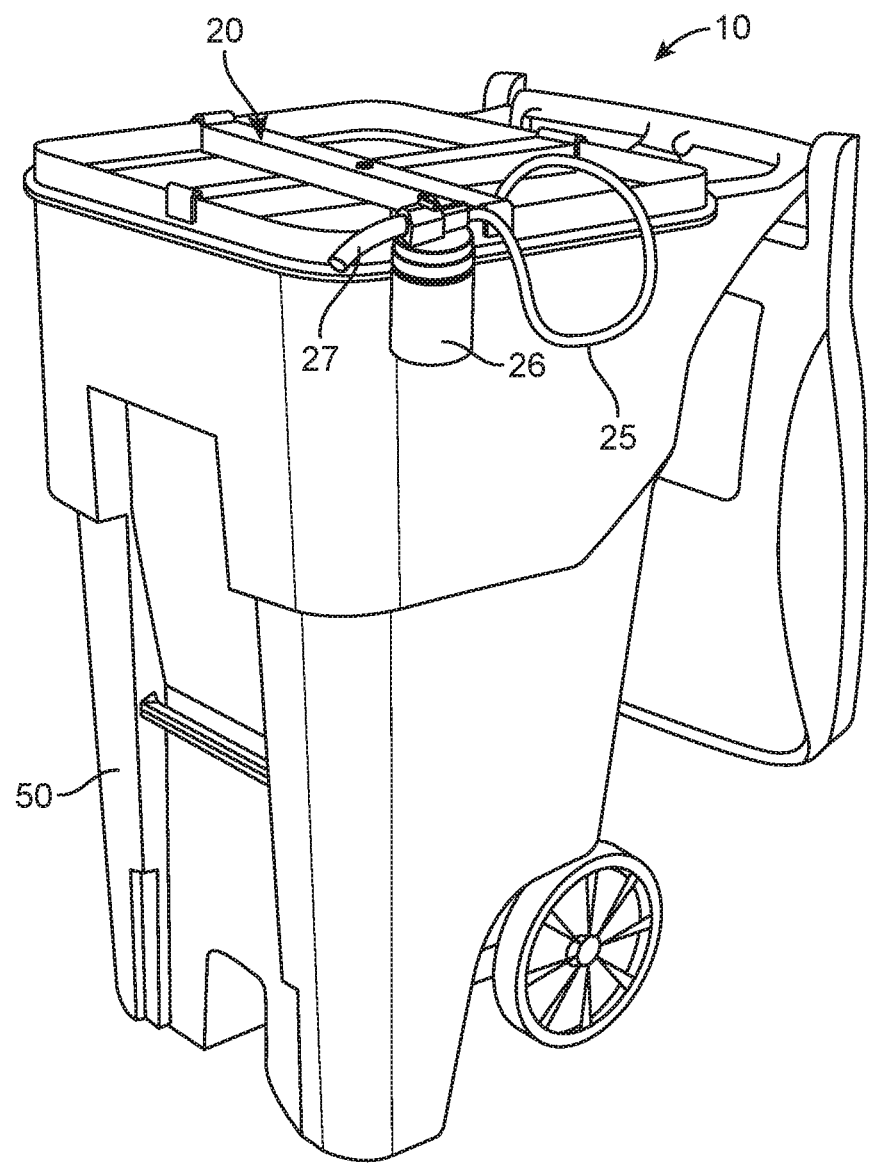
FIG. 1 represents an isometric operational view of a receptacle cleaning system 10 mounted to a trash receptacle 50 in accordance to an embodiment of the present invention.

Referring now to the drawings, where the present invention is generally referred to with numeral 10, it can be observed a system for a receptacle cleaning device 10 which basically includes an attachment assembly 20 and an arm assembly 40.

Figure 2:
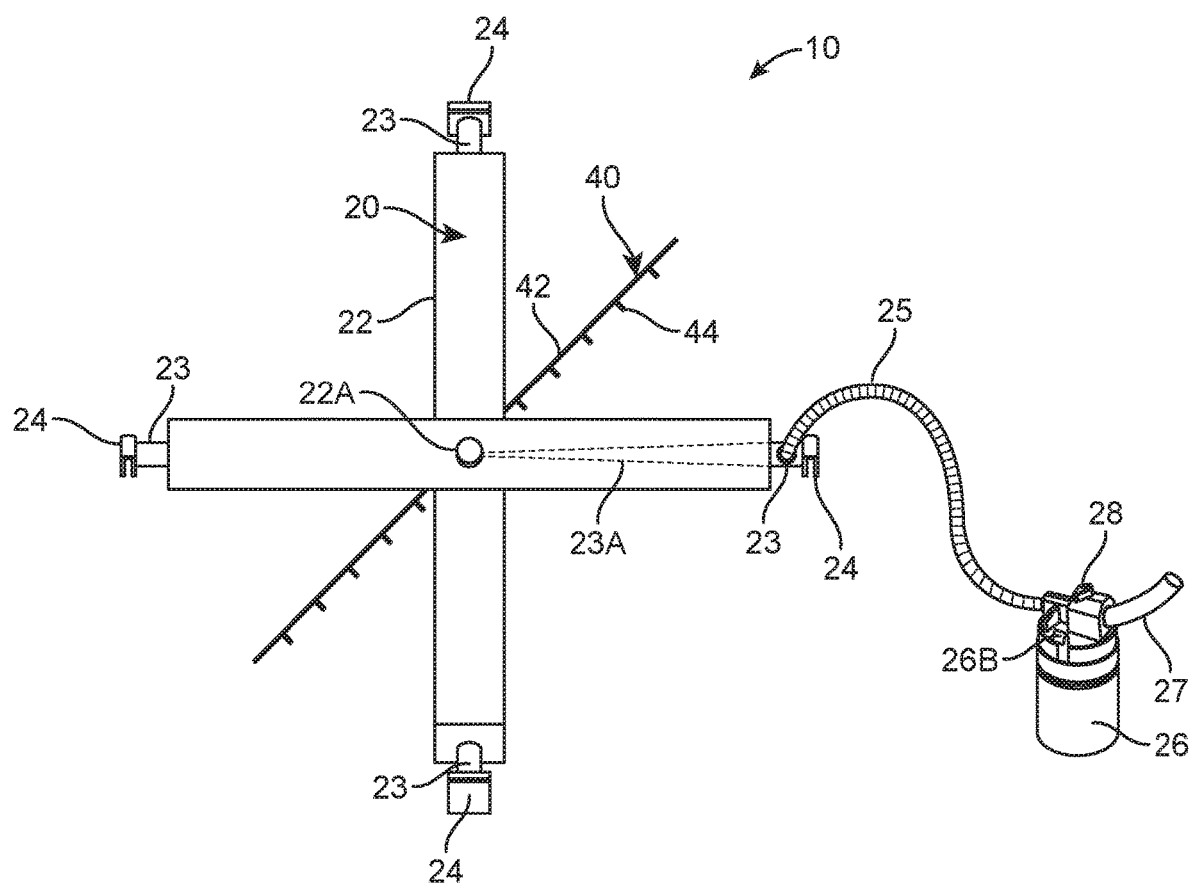
FIG. 2 shows an isometric top view of receptacle cleaning device 10 depicting attachment assembly 20 in accordance to an embodiment of the present invention.
Figure 3:
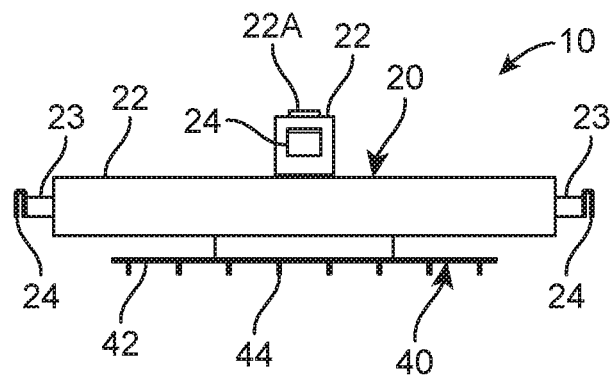
FIG. 3 illustrates a side view of receptacle cleaning device 10 depicting arm assembly 40 in accordance to an embodiment of the present invention.
Figure 4:
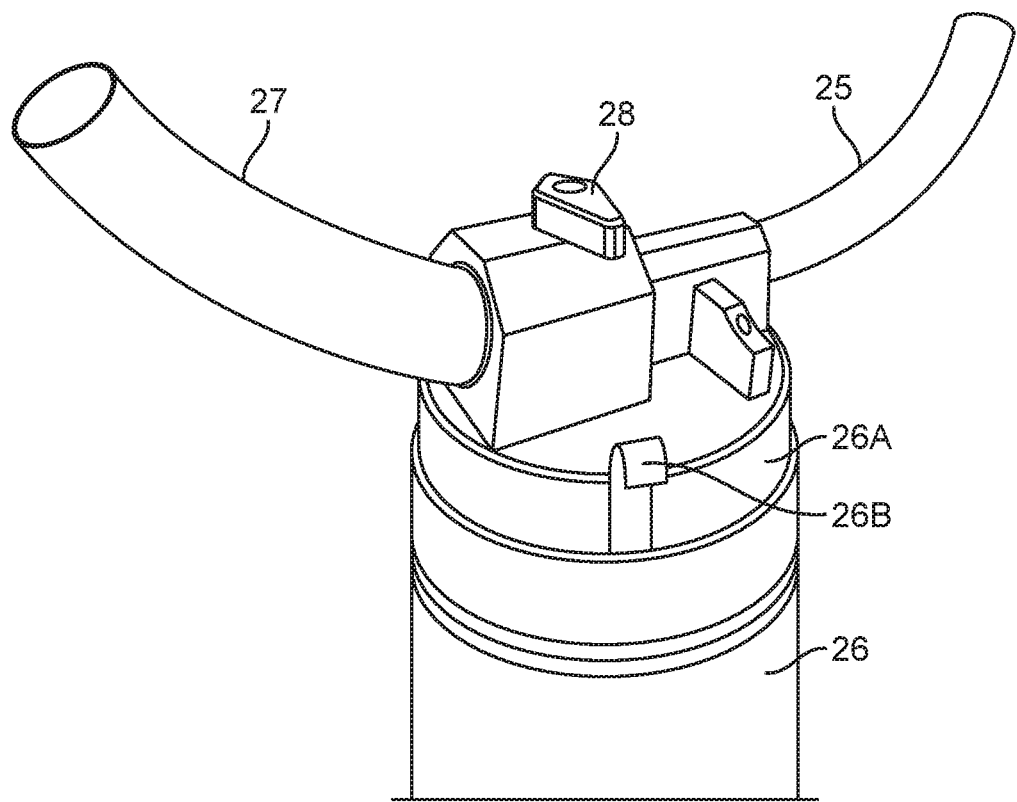
FIG. 4 is a representation of an enlarged view of compartment 26 connecting tube 25 and hose 27 in accordance to an embodiment of the present invention.
Figure 5:
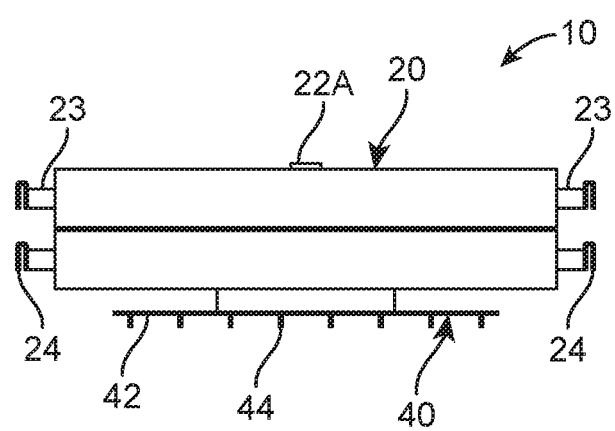
FIG. 5 shows a side view of receptacle cleaning device 10 in a collapsed configuration in accordance to an embodiment of the present invention.

Attachment assembly 20 includes an attachment member 22 which is configured to be mounted over a top end of a trash receptacle 50. In the present embodiment, trash receptacle 50 may be represented as most standard trash receptacles of most dimensions. Attachment member 22 is provided in a cross shaped configuration having a vertical portion and a horizontal portion joined together in a perpendicular connection. Additionally, the vertical and horizontal portion of this attachment member may have identical dimensions. In one embodiment, the vertical and horizontal portions are rotatably joined at a central point having one portion mounted to another. The central point may include a pin 22A that joins the vertical and horizontal portions and enables the rotation of attachment members 22 when being collapsed for packaging purposes or storage purposes after use. It is observed in FIG. 2, attachment assembly having a cross shaped configuration with a plus or "+" shape. The rotatable configuration of attachment assembly 20 allows attachment members 22 to rotate in order to achieve a minus or "−" shape. This shape provides attachment assembly 20 with a collapsed configuration. This configuration allows for the device to be easily stored in various locations and packaged for ease of distribution.

Attachment member 22 further includes adjustable arms 23 extending outwardly from each of four ends of attachment member 22. In one embodiment, adjustable arms 23 are telescopic in nature and extend outwardly from attachment member 22. Each of adjustable arms 23 may be independently adjusted to extend to and edge of trash receptacle 50. This configuration allows the attachment member 22 to be placed over a trash receptacle 50 of most dimensions. Additionally, each end of adjustable arms 23 includes a clamp 24 which grasps the edge of trash receptacle 50 in order to create a secure connection. In one implementation, clamp 24 is made of a rubber material to aid in maintaining a high coefficient of friction when mounted onto trash receptacle 50. The present invention may also feature other forms of attachment members coupled to adjustable arms 23. FIG. 1 depicts the receptacle cleaning device 10 configured to be mounted onto a traditional trash receptacle.

Attachment assembly 20 further includes a tube 25 which extends into one of adjustable arms 23. In one embodiment, tube 25 is provided as a clear flexible tube which allows for a user to observe the contents that is being transported within the tube. Tube 25 extends into attachment member 22 to create a fluid communication therein. In the present embodiment, tube 25 extends into only one of adjustable arms 23 and is in fluid communication with an inner channel 23A extending within the adjustable arms 23 and attachment member 22. Inner channel 23A is then in fluid communication with arms assembly 40 and serves to provide water therethrough. In one embodiment, inner channel 23A may be provided as a tapered channel which tapers within adjustable arms 23 and towards a center of attachment members 22. The tapering configuration creates water pressure as water travels through inner channel 23A into arm assembly 40 in order to provide a more thorough cleaning within trash receptacle 50.

Additionally, tube 25 includes a compartment 26 coupled to one end. In one implementation, compartment 26 is a housing that serves as a connection point between tube 25 and a hose 27. Hose 27 may be provided as any traditional water hose found in an individual's home to supply water to the system. Compartment 26 further includes a cavity therein which receives a cleaning solution that is inserted by a user. This cleaning solution may be provided in many forms and is not limited to any type of cleaning solution. Additionally, the cleaning solution is may also be a disinfectant solution configured to remove harmful bacteria. In one implementation, a solid cleaning pod is inserted within compartment 26. In another implementation, a user may fill compartment 26 with any desired liquid soap. It should further be understood, that any form of disinfectant or cleaning aid may be inserted within compartment 26 to aid in the cleaning of trash receptacle 50. In yet another embodiment, a crystal type cleaning solution is inserted within compartment 26.

Compartment 26 may further include a cap 26A which serves as a connection point that receives hose 27 and tube 25. Additionally, cap 26A may be provided as a tapered member which tapers inwardly towards the connection point for tube 25. This tapering configuration provides water pressure to the system which allows the water supplied by hose 27 to more effectively mix in with the cleaning solution within compartment 26. Furthermore, cap 26A may further include a valve 28 mounted to a top end. Valve 28 allows the user to configure a waterflow in an "ON" and "OFF" position. In the "ON" position, water flow is configured to travel through cap 26A and into compartment 26. In the "OFF" position, a user is able to block the flow of water to the system. In other embodiments, valve 28 may be configured to have other settings that may allow a user to modify the amount of water pressure being introduced into compartment 26.

Compartment 26 may further include a hook 26B mounted to a side of the compartment 26. In one embodiment, hook 26B is any suitable hook member that allows compartment 26 to be mounted on various locations for easy access. In one implementation, hook 26B may be used to mount compartment 26 onto the top edge of trash receptacle 50 as seen in FIG. 1. This will allow compartment 26 to hang on the receptacle rather than dangling freely. Additionally, it will allow a user to visually observe how much cleaning solution is left within the compartment and allow the process of attaching and detaching hose 27 to be an easier process for a user. Other implementations may feature hook 26B mounted onto a railing or fence which may be provided near trash receptacle 50.

Once the connection point between, adjustable arms 23, compartment 26, and hose 27 has been established, and the cleaning solution inserted, water is then introduced into the system. The water from hose 27 then travels into compartment 26 to then mix in with the cleaning solution therein. The mixture formed within compartment 26 then travels through tube 25 which is then fed into inner channel 23A of adjustable arm 23 of attachment member 22. In one embodiment, compartment 26 is made of a clear material to allow a user to observe the mixture of water and cleaning solution therein. The clear material also allows a user to visually measure the amount of cleaning solution therein to help the user identify when it is time to refill the cleaning solution within compartment 26. Attachment assembly 2o is then in fluid communication with arm assembly 40 which supplies the mixture to the interior of trash receptacle 50.

Arm assembly 40 includes a spinning arm 42 which is mounted to the bottom end of pin 22A. In one embodiment, spinning arm 42 is provided as a singular elongated rectangular member having a predetermined length that is rotatably mounted to attachment member 22. Additionally, the predetermined length of spinning arm 42 may be a length that is equal to or less than a length of attachment member 22. Furthermore, spinning arm 42 may be a hollow member to allow for the flow of water therein. The water mixed with cleaning solution that is received by tube 25 is fed into spinning arm 42 through the fluid communication system of attachment member 22. Spinning arm 42 further includes a plurality of nozzles 44 which are mounted to a bottom end. The water and cleaning solution mixture are then dispensed through these nozzles at a high pressure to clean the interior of trash receptacle 50. Spinning arm 42 is further configured to spin in a full three-hundred-and-sixty-degree motion while cleaning trash receptacle 50. The momentum resulted in the fluid transportation of the water and cleaning solution mixture result in the rotation of spinning arm 42. Plurality of nozzles 44 may configured in various angles and have perforations of variable shape. This ensures that the water sprayed thereout covers the entire inner surface of trash receptacle at a sufficient pressure to be thoroughly cleaned. In another implementation, spinning arm 42 may be provided absent of plurality of nozzles 44. In this implementation, water is dispensed through a plurality of holes, that have been drilled into spinning arm 42. These holes may be varying in size and configured to create water pressure as water exits spinning arm 42.

The foregoing description conveys the best understanding of the objectives and advantages of the present invention.

Different embodiments may be made of the inventive concept of this invention. It is to be understood that all matter disclosed herein is to be interpreted merely as illustrative, and not in a limiting sense.

What is claimed is:

1. A system for a receptacle cleaning device, comprising:
   a) an attachment assembly including an attachment member having a cross shaped configuration with four ends, four adjustable arms wherein each adjustable arm is mounted to one of said four ends, wherein said four adjustable arms extend outwardly and away from said attachment member, each of said four adjustable arms having a distal end including a clamp, a tube mounted to one of said four adjustable arms forming a fluid connection with said attachment member, a compartment mounted to said tube forming a connection point with a hose, wherein said compartment receives a cleaning solution therein, wherein said hose introduces water within said compartment to form a mixture with said cleaning solution, wherein said mixture travels through said tube and flows into said attachment member; and
   b) an arm assembly including a spinning arm mounted to a bottom end of said attachment member, wherein said spinning arm is rotatably mounted to said bottom end, wherein said spinning arm includes a plurality of nozzles which dispense said mixture thereout.

2. The system for a receptacle cleaning device of claim 1 wherein said attachment member includes a vertical portion and a horizontal portion having an equal shape and size.

3. The system for a receptacle cleaning device of claim 1 wherein said clamp of each of said four adjustable arms receives an upper edge of a trash receptacle.

4. The system for a receptacle cleaning device of claim 1 wherein said clamp of each of said four adjustable arms is made of a rubber material.

5. The system for a receptacle cleaning device of claim 1 wherein said tube is a clear flexible tube.

6. The system for a receptacle cleaning device of claim 1 wherein said cleaning solution is a disinfectant solution in the form of a cleaning pod or a liquid soap.

7. The system for a receptacle cleaning device of claim 1 wherein said tube includes a switch including an "on" position and an "off" position.

8. The system for a receptacle cleaning device of claim 1 wherein said spinning arm includes a length equal to or smaller than a length of said attachment member.

9. The system for a receptacle cleaning device of claim 1 wherein said plurality of nozzles are placed in an angled configuration.

10. The system for a receptacle cleaning device of claim 1 wherein said one of said four adjustable arms includes an inner channel extending therein.

11. The system for a receptacle cleaning device of claim 1 wherein said compartment further includes a hook.

* * * * *